United States Patent [19]
West et al.

[11] Patent Number: 5,830,509
[45] Date of Patent: Nov. 3, 1998

[54] MICROPARTICLE COMPLEXES WITH 2-AMINO-1-PHENYLPROPANOL MATERIALS

[76] Inventors: Daniel David West, 1 Warren Ct., Rockport, Mass. 01966; Richard Breitbarth, deceased, late of Whippany, N.J.; by Amy Martrildonno, administratrix, 106 Woodrow St., Middlesex, N.J. 08846

[21] Appl. No.: 859,956

[22] Filed: May 21, 1997

Related U.S. Application Data

[63] Continuation-in-part of Ser. No. 597,972, Feb. 7, 1996, Pat. No. 5,785,977, and Ser. No. 780,573, Jan. 8, 1997.

[51] Int. Cl.$^6$ ........................................... A61K 9/14
[52] U.S. Cl. ........................ 424/489; 414/434; 414/485; 414/401; 514/649
[58] Field of Search ..................... 424/401, 489, 424/485, 434; 514/649

[56] References Cited

U.S. PATENT DOCUMENTS 5,521,220  5/1996  O'Neill ..................... 514/649

Primary Examiner—Thurman K. Page
Assistant Examiner—D. Faulkner
Attorney, Agent, or Firm—Evelyn M. Sommer

[57] ABSTRACT

Microparticulate carrier materials for a large and varied group of pharmaceutical and cosmetic agents are disclosed. Microdispersions of such carrier materials charged with at least one isomer or derivative of 2-amino-1-phenylpropanol are also described. The microdispersions can be formulated for oral, parenteral, topical, inhalation and suppository administration. The formulations have varied uses depending on the pharmaceutical and or cosmetic agent utilized. The microparticles are suitably charged particles of silica, alumina, boron, charcoal and the like and have a particle size of about 3 to about 250 $\mu$m. The pharmaceutical and cosmetic active materials complex with the microparticles. The liquid carrier for the microparticles include water, propylene glycol, alcohols such as methanol, ethanol and propanols, and dimethyl sulfoxide. The resulting dispersions are believed to be similar to isotonic saline and mimic body fluids which makes the dispersions very physiologically compatible thereby aiding and speeding the delivery of the agents across membranes and to the afflicted tissue. Methods of using these microdispersions and the containing the same are also disclosed.

19 Claims, No Drawings

MICROPARTICLE COMPLEXES WITH 2-AMINO-1-PHENYLPROPANOL MATERIALS

This application is a continuation-in-part of Ser. No. 08/597,972 now U.S. Pat. No. 5,785,977, filed Feb. 7, 1996 and Ser. No. 08/780,573 filed Jan. 8, 1997.

The present invention is directed to a combination of a microparticle carrier material with an isomer or derivative of 2-amino-1-phenylpropanol. More particularly, the invention is directed to microparticles, the electrical surface charge of which has been adjusted so that they can serve as carrying agents for an isomer or derivative of 2-amino-1-phenylpropanol, the resultant products and methods of making and using these microparticulate materials. Still more particularly this invention involves microdispersions of microparticles, an isomer or derivative of 2-amino-1-phenylpropanol, which microdispersions remain stable for long periods of time and which are useful as therapeutic sympathomimetic agents by humans and animals. These combinations can be successfully used in treating obesity, depression, and other conditions.

BACKGROUND—DISCUSSION OF PRIOR ART

Sympathomimetic agents have long been used in medicine for their effects on the blood vessels and the peripheral and central nervous system. The present invention relates to compounds having their effect primarily on the central nervous system which are derivatives of β-phenylthylamine.

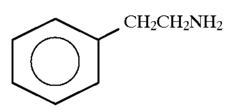

One such compound is the alpha methyl derivative commonly known as amphetamine.

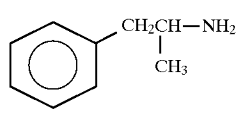

Amphetamines are important therapeutic compounds that have been widely used for many years in the form of various salts, isomers and derivatives. Specifically, amphetamines have been used as appetite suppressants to treat obesity, as CNS stimulants to treat depression and other psychogenic disorders, in the treatment of narcolepsy, epilepsy, post-encephalitic parkinsonism, and hyperkinetic syndromes in children who suffer from minimal brain dysfunction.

However, amphetamines are disfavored, partly due to their short-lived effectiveness (tolerance), but more because of the considerable abuse potential (addiction).

There is a great need for an effective appetite suppressing agent that is free from abuse liability and tolerance development as obesity remains a challenging problem because of its increasingly understood linkage to other serious disorders.

Amphetamine and its derivatives undergo a number of metabolic transformations catalyzed by enzymes in vivo. The presence of the alpha methyl group retards the rate of deamination by monoamine oxidase (MAO) enzymes and allows the transformation shown below to occur:

Amphetamine

Norephedrine 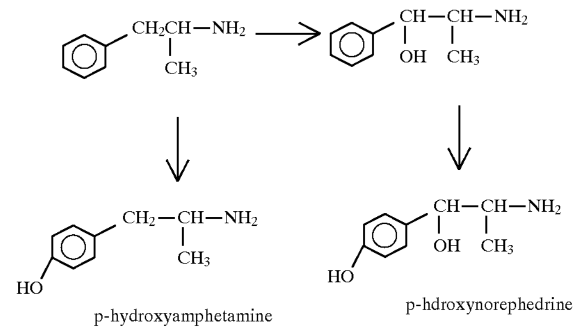 p-hydroxyamphetamine p-hdroxynorephedrine

The upper right compound—norephedrine—has proven to be relatively free of abuse liability and tolerance development, while still retaining some of the appetite suppressing properties of amphetamine. A racemic mixture of norephedrine—phenylpropanol amine (PPA)—has a somewhat stronger appetite suppressing effect than optically pure norephedrine due to the presence of the D-isomer. Phenylpropanol amine (PPA) has been widely used in non-prescription appetite suppressants.

Among the diasteromers, the D-isomer of norephedrine—D-pseudo norephedrine—has the greatest appetite suppressing effect, approaching that of amphetamine. Moreover, the D-isomer is relatively free of abuse and tolerance development. This compound has been marketed mostly in Europe under the names "Adiposetten" and "Amorphen" by the German companies, Reiss and Heumann, respectively. D-pseudo norephedrine occurs in nature in the leaves of the Kat plant, Catha Edulis Forsk, and Celastraceae (an evergreen shrub native to southern Arabia and Ethiopia). It is also found in smaller amounts in the South American tree Maytenus Krukonii A. C. Smith Celastraceae, and in the mother liquor from Ma Huang after the recovery of ephedrine.

All of the above compounds (including ephedrine itself) are not entirely free from undesirable sympathomimetic agent side effects. The above compounds can produce nervousness, insomnia, dizziness, restlessness, anxiety, tremors, hyperactive reflexes, and later weakness, fatigue, and general depression.

Cardiovascular effects may result in headache, hypothermia, tachycardia, arrhythmia, anginal pain, and sweating. Gastrointestinal effects may include dry mouth and nasal passages, metallic taste, nausea and vomiting, and diarrhea with abdominal cramps. In addition, chronic use may produce a form of paranoid psychosis. These compounds are generally contraindicated in cases of hypertension, heart disease, diabetes, kidney disease, and thyroid disorder. In an effort to overcome some of these drawbacks, Cook and Fellows of Smith Kline undertook considerable research dealing with amphetamines and similarly acting agents and filed for numerous patents including British patent No. 828,880 and U.S. Pat. No. 2,974,148 (1961), describing the use of isomers of methylenedioxyamphetamine (MDA) as ataractic and anorexigenic agents. While these compounds did eliminate many of the side effects, MDA proved to have an abuse liability equal to amphetamine and was included in the Controlled Substance Act of 1970.

The following table summarizes the pharmaceutical uses of 2-amino-1-phenylpropanols.

TABLE 1

Derivatives of 2-amino-1-phenylpropanol

| Phenylpropanol amine | R' | R" | Stereochemistry | Indication | Prod. Name |
|---|---|---|---|---|---|
| (DL-Norephedrine) | H | H | DL-erythro | sympathomimetic | Propadrine |
| L-Norephedrine | H | H | L-erythro | sympathomimetic | |
| D-Norpseudo ephedrine | H | H | D-threo | appetite suppressant | Adiposetten |
| Metaraminol | H | 3-OH | L-erythro | sympathomimetic | Aramine |
| p-Hydroxy norephedrine | H | 4-OH | D-L erythro | sympathomimetic | |
| Corbadrine | 3-OH | 4-OH | L-erythro | vasoconstrictor | Corefrine |
| Methoxamine | 2-OCH$_3$ | 5-OCH$_3$ | D,L-erythro | vasoconstrictor | Vasylox |

These compounds possess two asymmetric carbon atoms and exist as threo and erythro diastereoisomers. In addition, the threo and erythro forms each exist as D and L enantiomers, for a total of four possible stereoisomeric forms as shown in Table B below:

|  |  | Configuration | C1 | C2 | Relative Pressor Activity* |
|---|---|---|---|---|---|
| CH$_3$ | CH$_3$ | L erythro | S | S | 1.0 |
| H 2 NH$_2$ | H 2 NH$_2$ | D erythro | R | S | 0.33 |
| O 1 OH | HO 1 H | D threo | S | S | 0.2 |
| C$_6$H$_5$ | C$_6$H$_5$ | L threo | R | R | depressor |

*Relative to ephedrine.

The four stereo isomers, in general, produce different pharmacological responses. Thus, the threo forms and the D isomers tend to be more centrally active while the erythro forms and the L isomers tend to be more vasoactive. For example, the threo form of racemic 2-amino-1-phenylpropanol is active as an appetite suppressant [the D threo form (Adiposetten) is more active], but relatively weak as a vasoconstrictor or bronchial dilator. In contrast, the erythro form (Propadrine) and its L enantiomer (L-Norephedrine) exhibit powerful vasoconstrictor activity.

While some of the optical isomers have been separated, it is usually difficult and costly to do so. Moreover, mechanisms to prepare the optically pure isomers have not been available.

Mixed stereoisomers of 2-amino-1-phenylpropanol can be readily prepared by reacting benzaldehyde with nitroethane in the presence of an alkaline catalyst to produce 2-nitro-1-phenylpropanol which is then reduced to the amine. E.g., Hoover and Hass, *Journal of Organic Chemistry*, 12, 506, (1947). This reaction gives excellent yields at low cost. However, separating the stereoisomers produced by this reaction has not been satisfactory. As a result, heretofore, the only practical stereospecific synthesis of 2-amino-1-phenylpropanols involves the reduction of propiophenone derivatives to the racemic erythro diastereoisomers and fractional crystallization of the amine salt of an optically active acid.

The DL-erythro forms can be readily obtained from the appropriate propiophenone derivatives or by inversion of DL-threo derivatives. Since the pharmacological properties of the D and L isomers differ, it is desirable to separate the two, resulting in maximum therapeutic utility. While such potentially useful products can also be prepared, the difficulty of separating, i.e. "resolution", the isomers has prevented their development.

Specifically, the base is converted to a salt of an optically active acid. For example, the DL-base is reacted with a D-acid. This results in the formation of a mixture of D-base-D-acid and L-base-D-acid. These two salts differ in solubility. When the mixture is cooled and allowed to stand, the D-base-D-acid, typically being the less soluble, precipitates out of the solution first. By removing the precipitate at the appropriate time, the collected precipitate is largely the D-base-D-acid, while the L-base-D-acid remains in solution.

While purifying the optical isomers to some extent, substantial impurities often remain. Impurities are removed to some degree by fractional crystallization. The "pure" D and L bases are then liberated by adding a sufficient amount of an alkali to a solution of the "pure" salt to reach a pH above 7.

The above process is very tedious, time consuming, and inefficient. In addition, a base with the same configuration as the resolving acid is more easily separated and purified than the opposite enantiomer. Consequently, in practice, the desired isomeric base must be matched with an optically active acid of the same configuration to achieve maximum yields.

The optically pure derivatives of D-threo-2-amino-1-propanol function as therapeutic sympathomimetic agents which:

(a) have a lower tolerance development in the human body;

(b) are less likely to be abused; and (c) have fewer side effects.

As a result, as reported in application Ser. No. 08/780,573 there has now been reported a safe and effective alternative treatment for obesity, depression or other psychogenic disorders, narcolepsy, epilepsy, postencephalitic parkinsonism and hyperkinetic syndromes in children who suffer from minimal brain dysfunction, as well as numerous other disorders.

Ser. No. 08/780,573 discloses that reacting a benzaldehyde derivative with a nitroalkane in the presence of a tertiary amine forms the threo nitroalcohol formed. In contrast, when sodium hydroxide is used as the catalyst, a mixture of threo and erythro isomers results.

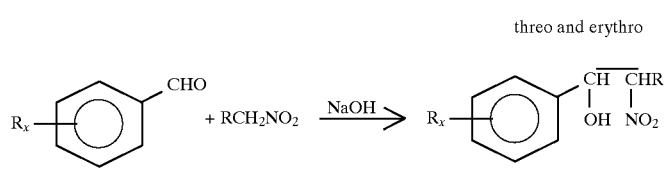

threo and erythro

-continued threo alone

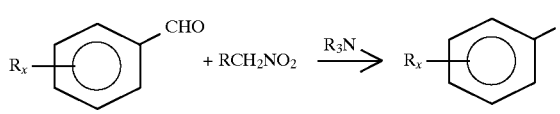

Benzaldehyde derivatives that react according to this scheme include: benzaldehyde and benzaldehydes containing halogen, hydroxy, alkyl and alkoxy groups, and combinations thereof, in the aromatic ring.

The nitro alkane can be nitroethane or nitropropane. The tertiary amines include trimethylamine, triethylamine, tributylamine, and others (®=alkyl).

The reaction is best conducted in an aqueous aliphatic alcohol.

The tertiary amine employed must be free of primary and secondary amines which interfere with the reaction. These can be removed from the commercial products by refluxing with acetic or phthalic anhydride followed by distillation.

In a preferred embodiment as disclosed in application Ser. No.08/780,573, a benzaldehyde derivative is reacted with nitroethane in the presence of triethylamine in aqueous ethanol. The mixture is allowed to react at room temperature for twenty-four hours. The mixture is then acidified with an organic acid since mineral acids tend to promote decomposition, as does heat. Excess solvents and reactants are evaporated and the nitroalcohol extracted.

The nitroalcohol can easily be reduced by catalytic hydrogenation or conventional reducing agents such as zinc and acid. Lithium aluminum hydride was found to work exceptionally well. The racemic threo isomers can readily be inverted to the racemic erythro isomers by reaction with acetic anhydride and thionyl chloride and hydrolysis. N-methyl derivatives can be prepared by adding an equimolecular amount of aqueous formaldehyde to the primary amine and reducing the Schiff base.

The use of a primary aliphatic alkylamine results in the formation of the dehydration product of the nitroalcohol—the beta-nitrostyrene. By employing a secondary or tertiary amine in the presence of water, nitrostyrene formation is completely eliminated. The use of a secondary or tertiary amine prevents the formation of a Schiff base amine, the necessary intermediary for nitrostyrene formation.

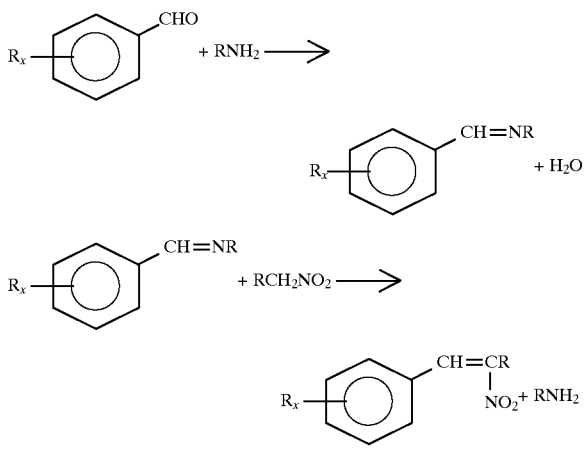

While the use of either the secondary or tertiary amine prevents nitrostyrene formation, only the tertiary amine results in stereospecificity.

The racemic threo isomer can readily be inverted to the racemic erythro isomers by reaction with acetic anhydride and thionyl chloride and hydrolysis.

The N-methyl derivatives can be prepared by adding an equimolecular amount of aqueous formaldehyde to the primary amine and reducing the Schiff base catalytically.

Instead of the usual fractional crystallization of the amine-acid salt, the method of resolving stereo isomers uses a novel phase transfer resolution. It was found that if the amine base is rapidly stirred with a mono alkali metal salt "of" a tartaric acid ester in a two-phase system of a hydrocarbon and water, a rapid and efficient resolution can be achieved.

Amine bases useful in that process are represented by the following formula:

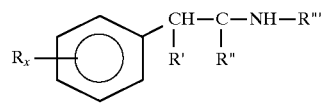

wherein R'=H, OH, or alkoxy; R"=H, or alkyl; R'''=H, OH, or alkyl; x=1–5 and $R_x$=H, halogen, hydroxy, alkyl, alkoxy groups, and combinations thereof. In a preferred embodiment at least one of $R_x$ is not H.

Sodium and potassium are each useful as the alkali metal of the alkali metal salt. Useful tartaric acid esters include dibenzoyl and ditoluoyl tartrate. Useful hydrocarbon phases may be aromatic (benzene, toluene, etc.) or halogenated aliphatic (dichloromethane, dichloroethane, etc.).

In a practical embodiment of the resolution method, a DL-2-amino-1-phenylpropanol derivative in dichloromethane is combined and stirred with dibenzoltartaric acid in water, and aqueous sodium hydroxide for from about one to three hours. The reaction mixture is then allowed to stand for the about same length of time. The dichloromethane phase is separated and dried over anhydrous magnesium sulfate. Evaporation gives the L-threo isomer in nearly quantitative yield. The aqueous phase is made alkaline with ammonia and extracted with dichloromethane. The dichloromethane extract is dried over anhydrous magnesium sulfate and evaporated to give the D-threo isomer in nearly quantitative yield.

Amphetamine has alpha and beta stimulant sympathomimetic activities and enhances the turnover rate of both norepinephrine and dopamine while depleting norepinephrine centrally.

The side effects of amphetamine and related compounds are mainly due to excessive beta receptor stimulation. Methamphetamine, for example, being a stronger beta stimulant than amphetamine, produces more pronounced cardiovascular effects. On the other hand, amphetamine has less beta activity than racemic amphetamine and causes fewer cardiovascular side effects.

The addition of a beta-hydroxy group to amphetamine reduces abuse liability and tolerance development, but does not reduce cardiovascular beta effects. Among the four possible isomers L-2-amino-1-phenylpropanol, the D threo isomer, has the greatest alpha/beta ratio and results in the fewest side effects.

The inventor of application Ser. No.08/780,573 found that the nuclear substitution of certain alkoxy or alkoxy alkyl groups to D-threo-2-amino-1-phenylpropanol results in an optimum alpha/beta ratio while still maintaining a minimal abuse liability and tolerance development. These compounds may be used advantageously as substitutes for amphetamine as they are a series of novel sympathomimetic agents with amphetamine-like activity, but having fewer side effects than PPA or the like, and little or no abuse liability and tolerance development.

These derivatives of D-threo-2-amino-1-phenylpropanol have the structure shown below:

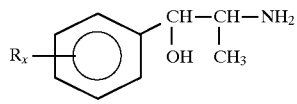

$R_{x,x=1-5}$=H, halogen, hydroxy, alkyl, alkoxy groups such as —CH$_3$O, —OCH$_2$O—, —CH$_3$, etc., and combinations thereof.

The alkoxy or alkoxy alkyl D-threo-2-amino- 1 -phenylpropanol are prepared by reacting an appropriately substituted benzaldehyde derivative with nitroethane in the presence of an alkaline catalyst and reducing the formed nitroalcohol. The resulting DL-threo aminoalcohol may then be resolved into the D-threo and L-threo isomers. Although the D isomers have the highest therapeutic index, the L and DL forms are not without pharmacological activity and are suitable for the uses herein disclosed.

The hydrochloride salts are preferably used, however any non-toxic pharmaceutically acceptable acid addition salts or the freebase itself may be employed. Examples of salts that may be used include the sulfate, phosphate, nitrate, citrate, acetate, lactate, tartrate, and benzoate. The salts are readily prepared by reacting the freebase with a stoichiometric amount of the desired acid in a suitable solvent such as ethanol, ether, ethyl acetate, acetone, water, or various combinations of solvents.

For example, hydrochloride salts of the bases can be prepared by dissolving the free base (about 1 mole) in anhydrous ether (500 ml.) and bubbling dry hydrogen chloride gas through the solution until the precipitation is completed. The hydrochloride salt precipitate is filtered with suction and dried. The salt is recrystallized from aqueous isopropanol.

As described in application Ser. No. 08/780,573, the products may be administered in all conventional pharmaceutical forms including tablets, hard and soft gelatin capsules, and ampules.

The following are of the amino phenylpropanols produced by the aforesaid procedures and which compounds are believed to be useful in the present invention: optically pure D-threo-2-amino-1-(3,4,5-trimethoxy) phenylpropanol and hydrochloride; optically pure D-threo-2-amino-1-(2,5 dimethoxy) phenylpropanol and hydrochloride; optically pure D-threo-2-amino- 1 -phenylpropanol; optically pure D-threo-2-amino-1-(3,4,5-trimethoxy) phenylpropanol and hydrochloride; optically pure D-threo-2-amino-1-(2,5 dimethoxy) phenylpropanol and hydrochloride; optically pure D-threo-2-amino-1-(3,4-methylenedioxy) phenylpropanol and hydrochloride; optically pure D-threo-2-amino-1-(3,4,5-trimethoxy) phenylpropanol and hydrochloride; and optically pure D-threo-2-amino-1-(2,5 dimethoxy) phenylpropanol and hydrochloride

DESCRIPTION OF THE INVENTION

According to the present invention, there are provided novel compositions of microparticles carrying on their surface an isomer or derivative of 2-amino-1-phenylpropanol. The invention, in addition provides pharmaceutical and cosmetic compositions containing the above novel materials and a pharmaceutically acceptable carrier therefore. In the preferred embodiments of the invention, the pharmaceutical composition is comprised of a composition of the invention in stable microdispersion form suitable for injection, oral ingestion or topical application.

The compositions of the present invention are believed to be effective in treating obesity, depression, and other conditions.

The microparticle carrier materials are more fully described in application Ser. No. 08/597,972.

The novel compositions comprising the complexed with the above discussed isomers and derivatives can be applied topically, parenterally or taken orally, rectally or vaginally depending on the active agent and its intended purpose. Moreover, it is now believed that the activity of the pharmaceutical agent is significantly enhanced so that materials that are normally effective only at toxic levels can now be administered at subtoxic levels and still be effective. In accordance with other embodiments of the invention, therapeutic agents that at present are administered parenterally, i.e., intravenously, intraperitoneally, and intramuscularly, can be converted into orally administered preparations.

The isomer or derivative of 2-amino-1-phenylpropanol is, in accordance with the invention, complexed with a microparticle, the surface of which microparticle is able to complex with the agent by ionic bonding. The success of utilizing such solid particles, depends largely on several key factors. The qualities of the ideal particles (matrix materials) are dependent on their very small, size, electrical potential, zeta potential, uniformity, spherical shape and rigid nature and their good flow properties. The particles should possess a supply of chemical groups, especially anionic groups, and thereby bond ionically to a variety of agents, especially agents with cationic groups. Moreover, the particles should be chemically stable to the conditions of coupling, adsorption and elution.

Until recently, almost all materials have been derivatives of cellulose, polystyrene or synthetic poly-amino acids, cross-linked dextrans, polyacrylamide gels and agarose. Although these insoluble non-metallic carriers are a diverse group, certain restrictions limit their usefulness to specific situations, e.g., cellulose's usefulness is limited by its fibrous and non-uniform character which impedes proper penetration of large molecules. Polystyrene, polyacrylamide and cross-linked dextran gels have low porosity. The beaded derivatives of agarose are ideal for use in some situations. The beads are uniform, small, stable and spherical and have a high capacity for substitution. However, the usefulness of these beads is limited by their temperature lability and by their tendency to break down.

The carriers preferred for use herein include silica, charcoal, alumina and boron microparticles.

Microparticles derived from silica and boron materials are the preferred, and most widely used, microparticles. The silica materials are available commercially as porous granules of high quality, silica permeated by interconnecting pores of uniform and precisely controlled sizes. While such materials are insoluble and largely unaffected by changes in their immediate environment, pH and ionic strength changes may affect the microparticles charge, and thus its ability to bind the desired agents. It is preferred that the microparticles have a substantial negative charge at physiological pH and physiological ionic strength. The microparticles used herein are also resistant to microbial attack and can be sterilized by disinfectants or heating. The surface of useful silica particles usually provides a plurality of hydroxyl groups which exhibit a negative charge in aqueous solution.

Silica particles are available in at least two types, macroparticulate and microparticulate. The macroparticulate silica particles typically have a mean particle diameter greater than about 250 μm and are rather porous. The microparticulate silica particles typically used herein have a mean diameter of greater than about 3 μm and are also usually porous. Desirably these microparticles have a mean diameter of less than about 100 μm, more desirably less than about 14 μm, and more desirably less than about 10 μm. Useful silica microparticles usually also have either spherical or moderately irregular shapes. Microparticulate silica particles display the highest efficiencies as well as the greatest loading capacity. The silica particles can be used directly or modified by coating or chemically bonding an active phase onto the silica particle's surface.

Alumina (aluminum oxide) $Al_2O_3$ particles are also suitable for use herein, even though aluminum is a metal. Alumina occurs in nature and is a white crystalline very hard powder that is insoluble in water, but which displays nonmetallic properties even though it comprises a metal (thus, for the purposes of this disclosure, a material is nonmetallic if its properties are nonmetallic even if it comprises one or more metallic ions). When activated, it can be used for attachment of other molecules. Alumina microparticles have an average particle size of about 7 μm.

Similarly to alumina, charcoal (such as that sold under the trade name Darco) is a water insoluble nonmetallic microparticulate material that can be used for attachment of other molecules Boron compounds, such as boric acid, sodium borohydride, boric anhydride and sodium borate can also be used effectively.

The particle sizes for silica described herein are useful as guidelines for selecting particle sizes for other microparticulate materials that are useful in the present invention.

The choice of microparticulate material is dependent on the specific conditions that may be unique for each application. However silica microparticles are preferred.

The particles may already carry the desired electrical charge or they can be modified using the conventional techniques so that they exhibit the appropriate charge. Such techniques include exposure to corona discharge, high shear intense grinding and chemical treatment.

The bonding capacity of the particles may be further increased by applying to the particles' surfaces a surfactant coating, for example a Tween (such as Tween 20 [polyoxyethylene sorbitan monolaurate] or Tween 80 [sorbitan mono-oleate polyoxyethylene]), an alkylbenzene sulfonate, polyethylene glycol, ethoxypolyethylene glycol or an oxyethylenated glycol surfactant. Desirably the surfactant is a Tween.

The composition of the present invention the final product formed by complexing the isomer or derivative of 2-amino-1-phenylpropanol with the microparticles can be applied as a liquid using water or propylene glycol as the carrier, or it may be in the form of a gel, cream, liquid or spray. Additionally, the composition of the present invention may be adapted for parenteral, topical, oral, nasal, vaginal or suppository administration.

Desirably, the microparticles carry a positive charge and are of a particle size less than 100 μm.

To apply a coating to the microparticles, the microparticles are introduced into a vessel containing water and which has been provided with a high shear mixer. A surfactant, desirable a pharmaceutical grade surfactant, is then introduced and the resultant mixture subjected to strong agitation. The isomer or derivative of 2-amino-1-phenylpropanol can be directly introduced into this same mixing vessel when the coating operation is complete and the agitation continued for forming the final product.

The surfactant is preferably added in an amount from about 10 to about 15% by weight wherein a total of 100% by weight of the composition is obtained and preferably in a range of about 3 to about 10% by weight of the total composition in the mixing vessel.

The particle and amino-1-phenylpropanol isomer or derivative are combined under mixing sufficient to complex the carrier particles with the amino-1-phenylpropanol isomer or derivative to provide a microdispersion of the complex so formed. In addition, any of the well-known pharmaceutically acceptable carriers, excipients and/or diluents may be combined with the compositions of the present invention in a well known manner. Suitable diluents include, for example, water, polyethylene glycol, isopropyl myristate, magnesium stearate, calcium stearate, magnesium carbonate, calcium carbonate, magnesium silicate and mineral oil. The pharmaceutical composition may be in any form suitable for topical use, such as an ointment, gel, or cream. Conventional coloring, fragrance and preserving agents may also be provided.

The effective dosage of the compositions of the present invention is believed to be much lower than would be expected in light of the prior art, suggesting that the agents have unexpectedly high efficacy in this form. While the compositions may be used undiluted, the effective concentration for most topical applications can be as little as 0.01%, by weight. However, the compositions preferably contain from about 0.5% to about 20%, more preferably from about 1% to about 10%, by weight active ingredient. Topical compositions containing about 2% to about 3% of active ingredient appear to be particularly effective.

For systemic use, such as intravenous, intramuscular, or intraperitoneal injection, the compositions may similarly contain from about 0.01% to about 99% active ingredient, by weight. Preferred systemic compositions contain from about 0.05% to about 20% active ingredient, by weight.

The effective dosage of the compositions of the invention, when administered orally, must take into consideration the diluent, preferably water and the intended purpose sought to be achieved. The compositions preferably contain 0.05% to about 75% by weight active microparticles and preferably about 0.1% to about 50% by weight. When the compositions are ingested, desirably they are taken on an empty stomach.

The present invention is also suitable for systemic and localized injection of the compositions disclosed herein, including intravascular, intramuscular, subcutaneous, intraperitoneal, and other injection techniques. Such injection may be used for treatment of viral, fungal and bacterial infection.

Pharmaceutical compositions of the present invention can also be administered as an aerosol, for example, as a spray or nebulizer solution, or as a suppository. In such cases, the inventive microparticle-agent complexes are combined with the conventional other components for the corresponding means of administering the agent.

There is no evidence that the microparticles of the present invention are toxic in topical, systemic and oral use at the levels described herein.

A preferred method of producing the basic compositions comprises the following steps: water or other suitable diluent and, desirably, a surfactant, for example Tween 20 or 80 are continuously stirred in a mixing vessel provided with a homogenizer (a high shear mixer such as a Greerco). The microparticles having a suitable surface charge are then added, preferably ionically charged silica particles having a particle size of about 3 to 10 μm in an amount of preferably 7.5 to 20% by weight and most preferably 10–15% by weight. The active agent is then added so that a final concentration of a pharmaceutical amount of active agent will be realized and the resultant mixture stirred at high speed to form a stable microdispersion of all of the components. The compositions (microdispersions) can also include a suitable buffer, a preservative, a coloring agent, flavoring agent or any other conventional adjuvants for the intended mode of application and end use.

The following examples are give in order to more completely illustrate the invention, but are not to be construed as limiting the scope thereof.

EXAMPLE 1

Silica microparticles having a particle size of about 3 to about 10 μm, and a negative surface charge are introduced into a Greerco mixer containing 88% water and 12% Tween 20. The microparticles are present in an amount of 14% by weight. After intensive stirring of this mixture for 25–35 minutes, D-threo-2-amino-1-(3,4-methylenedioxy) phenylpropanol, 1% by weight, is added to form a stable microdispersion.

EXAMPLE 2

Example 1 is repeated using negatively charged alumina microparticles having a particle size of about 5–10 μm.

EXAMPLE 3

Silica microparticles having a particle size of about 3 to about 10 μm, and a negative surface charge are introduced into a Greerco mixer containing 88% water and 12% Tween 20. The microparticles are present in an amount of 14% by weight. After intensive stirring of this mixture for 25–35 minutes, D-threo-2-amino-1-(3,4-dimethoxy) phenylpropanol, 1% by weight, is added to form a stable microdispersion.

EXAMPLE 4

Silica microparticles having a particle size of about 3 to about 10 μm, and a negative surface charge are introduced into a Greerco mixer containing 88% water and 12% Tween 20. The microparticles are present in an amount of 14% by weight. After intensive stirring of this mixture for 25–35 minutes, D-threo-2-amino-1-(2,5-dimethoxy) phenylpropanol, 1% by weight, is added to form a stable microdispersion.

EXAMPLE 5

Silica microparticles having a particle size of about 3 to about 10 μm, and a negative surface charge are introduced into a Greerco mixer containing 88% water and 12% Tween 20. The microparticles are present in an amount of 14% by weight. After intensive stirring of this mixture for 25–35 minutes, D-threo-2-amino-1-(3,4,5-trimethoxy) phenylpropanol, 1% by weight, is added to form a stable microdispersion.

The afore referenced applications Ser. Nos. 08/597,972 and 08/780,573 are hereby incorporated in their entireties.

It is claimed:

1. A stable composition of a microdispersion of microparticles having a particle size of about 3 to about 250 μm, said microparticles carrying a negative surface charge, in a liquid carrier suitable for administering an active agent to an organism complexed with an active agent selected from the group consisting of an isomer or derivatives of 2-amino-1-phenylpropanol.

2. A stable composition according to claim 1 wherein said microparticles have a particle size of about 3 to about 14 μm.

3. A stable composition according to claim 1 wherein said microparticles are selected from the group consisting of silica, alumina, boron, and charcoal particles.

4. A stable composition according to claim 1 wherein said microparticles are selected from the group consisting of silica and alumina microparticles.

5. A stable composition according to claim 1 wherein said microparticles are silica microparticles.

6. A stable composition according to claim 1 wherein said liquid carrier is water.

7. A stable composition according to claim 1 wherein said liquid carrier is propylene glycol.

8. A stable composition according to claim 1 further comprising a surfactant.

9. A stable composition according to claim 8 wherein said surfactant is a member selected from the group consisting of Tween 20, Tween 80, alkylbenzene sulfonates, polyethylene glycols, ethoxylpolyethylene glycols and oxyethylenated glycols.

10. A stable composition according to claim 8 wherein said surfactant is a member selected from the group consisting of Tween 20 and Tween 80.

11. A method of medical treatment for a medical condition, said condition being selected from the group consisting of obesity and depression, said method comprising administering to the subject having said condition a pharmaceutically effective amount of a respective composition of a microdispersion of microparticles having a particle size of about 3 to about 250 μm, said microparticles carrying a negative surface charge, in a suitable liquid carrier complexed with an active agent selected from the group consisting of isomer or derivative of 2-amino-1-phenylpropanol.

12. A therapeutic preparation comprising a microdispersion of microparticles having a particle size of about 3 to about 250 μm, said microparticles carrying a negative surface charge, in a suitable liquid carrier and an active agent consisting of an optically pure member of the group consisting of threo-2-amino-1-phenylpropanol and acid addition salts of threo-2-amino-1-phenylpropanol, said preparation of said optically pure compound effective to produce sympathomimetic activity, said threo-2-amino-1-phenylpropanol having the following formula;

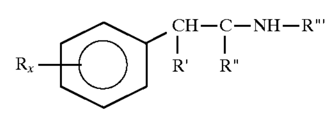

whereby: $R_x$=hydrogen, hydroxy, halogen, alkyl, or alkoxy groups, x=1–5, provided at least one $R_x$ is not hydrogen, and R', R" and R"' each=hydrogen, hydroxy, halogen, alkyl, or alkoxy groups.

13. The therapeutic preparation according to claim 12 in which said threo-2-amino-1-phenylpropanol and acid addition salts of threo-2-amino-1-phenylpropanol are D-threo isomers.

14. The therapeutic preparation according to claim 12 in which said threo-2-amino-1-phenylpropanol and acid addition salts of threo-2-amino-1-phenylpropanol are L-threo isomers.

15. The therapeutic preparation according to claim 12 in which said threo-2-amino-1-phenylpropanol and acid addition salts of threo-2-amino-1-phenylpropanol are DL-threo isomers.

16. The therapeutic preparation according to claim 12 in which said threo-2-amino-1-phenylpropanol and acid addition salts are threo-2-amino-1-phenylpropanol are D-threo-2-amino-1-(3,4-dimethoxy) phenylpropanol and hydrochloride.

17. The therapeutic preparation according to claim 12 in which said threo-2-amino-1-phenylpropanol and acid addition salts of threo-2-amino-1-phenylpropanol are D-threo-2-amino-1-(3,4-methylenedioxy) phenylpropanol and hydrochloride.

18. The therapeutic preparation according to claim 12 in which said threo-2-amino-1-phenylpropanol and acid addition salts of threo-2-amino-1-phenylpropanol are D-threo-2-amino-1-(2,5-dimethoxy) phenylpropanol and hydrochloride.

19. The therapeutic preparation according to claim 12 in which said threo-2-amino-1-phenylpropanol and acid addition salts of threo-2-amino-1-phenylpropanol are D-threo-2-amino-1-(3,4,5-trimethoxy) phenylpropanol and hydrochloride.

* * * * *